(12) United States Patent
Khalfan

(10) Patent No.: US 6,335,501 B1
(45) Date of Patent: Jan. 1, 2002

(54) OPTICAL PAPER SORTER

(75) Inventor: Zaheer Khalfan, Scarborough (CA)

(73) Assignee: Eco-Shred Ltd., Mississauga (CA)

( * ) Notice: Subject to any disclaimer, the term of this patent is extended or adjusted under 35 U.S.C. 154(b) by 0 days.

(21) Appl. No.: 09/497,663

(22) Filed: Feb. 4, 2000

(51) Int. Cl.[7] .............................. B07C 5/342; B07C 5/00
(52) U.S. Cl. ...................... 209/582; 209/581; 209/587
(58) Field of Search ............................ 209/580, 581, 209/582, 587, 638, 639, 932; 356/406, 407, 425; 250/559.16, 559.17, 559.18

(56) References Cited

U.S. PATENT DOCUMENTS

| | | | |
|---|---|---|---|
| 3,980,181 A | | 9/1976 | Hoover et al. |
| 4,278,538 A | * | 7/1981 | Lawrence et al. ........... 209/580 |
| 4,302,769 A | | 11/1981 | Andry et al. |
| 4,540,887 A | | 9/1985 | Minerd et al. |
| 4,592,090 A | * | 5/1986 | Curl et al. .......................... 382/7 |
| 4,731,663 A | * | 3/1988 | Kovalchick et al. ......... 358/101 |
| 4,812,904 A | * | 3/1989 | Maring et al. ................ 358/107 |
| 5,134,291 A | | 7/1992 | Ruhl, Jr. et al. |
| 5,315,384 A | * | 5/1994 | Heffington et al. ............. 348/93 |
| 5,692,622 A | | 12/1997 | Hergeth |
| 5,926,262 A | * | 7/1999 | Jung et al. ....................... 356/73 |
| 6,157,454 A | * | 12/2000 | Wagner et al. ................. 356/407 |

* cited by examiner

*Primary Examiner*—Donald P. Walsh
*Assistant Examiner*—Joseph C Rodriguez
(74) *Attorney, Agent, or Firm*—Dimock Stratton Clarizio; Mark B. Eisen

(57) ABSTRACT

An optical paper sorter that uses diffuse reflectance to identify a sheet of paper as either white or non-white. An illuminating fiber optic bundle carries light from a tungsten halogen lamp onto a sheet of paper. A receiving trifurcated fiber optic bundle collects light that is diffusely reflected from the sheet of paper. The light in each branch of the receiving fiber bundle is incident upon a detector after passing through a color filter positioned between the end of the fiber bundle and the detector. At each detector a specific isolated color (blue, green or red) in the visible range of the electromagnetic spectrum is incident, causing a photo electric voltage to be produced that is proportional to the intensity of the isolated component. A processor uses the mean and standard deviation of relative reflectances that are obtained based on the three voltage signals to determine if the paper is predominantly white or non-white. An air ejection device can be triggered to release a blast of air upon identifying the paper as white, or alternatively, non-white.

8 Claims, 3 Drawing Sheets

OPTICAL PAPER SORTER

BACKGROUND OF THE INVENTION

The present invention relates to an optical paper sorter, and in particular to a device and method for determining if a piece of paper is white or non-white.

In the paper recycling business, different grades of paper typically have different values, and thus there is a need to sort incoming recyclable paper products into various grades. Generally, the value of white paper exceeds the value of paper that is not white, and accordingly it is common to separate white recyclable paper from non-white recyclable paper. In the past, such sorting has been done manually, which tends to be expensive and has a varying degree of accuracy.

In other industries, the use of diffuse reflectance analysis has been applied to assist in sorting various types of work pieces, based on colour. For example, U.S. Pat. No. 4,278, 538 issued Jul. 14, 1981 to Lawrence et al discloses a sorting system for sorting telephone caps of uniform colour in which diffuse reflection from the caps is analyzed to determine the colour of the telephone caps. However, despite the use of diffuse reflectance analysis in other industries, it has not been adopted in the paper sorting industry. A unique problem faced in determining if a sheet of paper is white or non-white is that recyclable material, by its nature, generally includes printed or graphic information on its surface. Accordingly, in order to successfully distinguish between non-white and white paper products, an automated sorting system must be able to, with reasonable accuracy, distinguish white paper having printed and graphics material on its surface from non-white paper (which may also include white elements).

Accordingly, it is desirable to provide a device and method for determining the dominant colour of a piece of paper, and more particularly for determining whether a piece of paper can be categorized as white or non-white. It is also desirable to provide a device for redirecting pieces of paper depending on if they are white or non-white.

SUMMARY OF THE INVENTION

The present invention provides an optical sorter that measures the diffuse reflectance of an incident light beam on a piece of paper or other workpiece, and processes the measured values to catagorize the piece of paper or other workpiece as falling within one of two possible colour classifications.

According to one aspect of the invention, there is provided a device for determining the dominant colour of a workpiece. The device includes a light source for directing a beam of light at the workpiece to illuminate the workpiece, and an optical detection system for receiving light diffusely reflected off the workpiece, isolating three different spectral components of the reflected light, measuring the intensity of each of the three different spectral components and generating electrical signals representative of the intensity of each of the three different spectral components. A processor responsive to the electrical signals generated by the detection system is operable to determine a relative reflectance for each of the three spectral components, determine a mean of the three relative reflectances, determine a standard deviation of the three relative reflectances, and determine, by comparing the mean and standard deviation to predetermined threshold values, a probable dominant colour of the workpiece. Preferably, the optical detection system includes three photo detectors for receiving light diffusely reflected off the workpieces, and filters positioned between the photo detectors and the workpiece for isolating the reflected light into the three different spectral components such that each of the three photo detectors receives a different one of the spectral components and generates an electrical output representative of the intensity thereof.

Preferably, the processor is configured to determine the relative reflectance for each of the three spectral components by comparing the intensity of each of the three spectral components to predetermined reference intensity values obtained in respect of a reference workpiece of a known colour classification, and the processor is configured to determine the probable colour of the workpiece by classifying the workpiece as falling into one of two possible colour classifications, one of which is the known colour classification.

According to a further aspect of the invention, there is provided a paper sorting device for determining if the dominant color classification of a piece of paper is white or non-white, comprising a light source for directing a beam of light at the paper to illuminate it, and an optical detection system for receiving light diffusely reflected off the paper, isolating three different spectral components of the reflected light, measuring the intensity of each of the three different spectral components and generating electrical signals representative of the intensity of each of the three different spectral components. A processor responsive to the electrical signals generated by the detection system is operable to determine a relative reflectance for each of the three spectral components, determine a mean of the three relative reflectances, determine a standard deviation of the three relative reflectances, and determine, by comparing the mean and standard deviation to predetermined threshold values, whether the paper is white or non-white. Preferably, the wavelength ranges of the three spectral components are generally 400 nm–525 nm, 475 nm–650 nm, and 600 nm–800 nm, respectively. Conveniently, the device may include a conveyor system for advancing pieces of paper to and through a sampling station at which the light source is located, and an ejection device connected to said processor and being operable to selectively redirect a paper sample from the conveyor system, the processor being configured to cause the ejection device to redirect the paper sample from the conveyor system based on the determination of whether the paper sample is white or non-white.

According to still a further aspect of the invention, there is provided a method for classifying paper samples into one of two colour classifications, comprising the steps of directing a beam of visible light on the paper sample to illuminate a paper sample, measuring the intensity of three different spectral components in the light which is diffusely reflected off the paper sample, determining, based on the measured intensities, a relative reflectance for each of the three spectral components, determining a mean of the three relative reflectances, determining a standard deviation of the three relative reflectances, and comparing the mean and the standard deviation to predetermined values and classifying the paper sample as falling within one of two possible colour classifications based on the comparison results. Preferably, the two colour classifications are white and non-white and the first spectral component corresponds to the colour blue, the second spectral component corresponds to the colour green, and the third spectral component corresponds to the colour red.

DETAILED DESCRIPTION OF THE PREFERRED EMBODIMENTS

When a light beam strikes the surface of a piece of paper, both specular and diffuse reflections occur. For specular reflectance, the angle of incidence equals the angle of reflection, and the spectral distribution of the incident light energy is preserved. Specular reflectance determines the mirror like properties of a surface and is a measure of the surface gloss or shine. Some of the light beam that strikes the surface of the paper penetrates the first layer of the fibrous structure of the paper and experiences absorption and multiple internal reflection. The absorption of some, or all of the wave lengths in the light beam takes place as a result of absorbing elements or pigments contained within the paper. The wave lengths that are not absorbed experience scattering and multiple reflections and are finally re-emitted from the surface as diffuse reflection. This diffuse reflection is what is responsible for the colour, or colours, seen by the human eye. Diffuse reflectance is emitted in all directions and is not dependant on the direction of the incident light beam.

Figure 1:
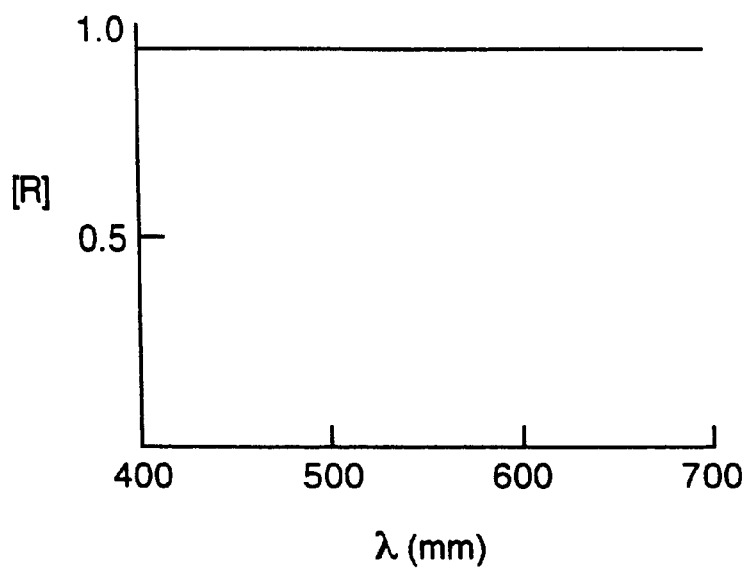
FIG. 1 is a graph showing the absolute reflectance of a perfect diffuser.

Objects that are white in colour appear white when viewed under normal light because almost all the light that is incident gets diffusely reflected from the surface of the object. The perception of the colour of the object as "white" is equivalent to preserving the integrity of the incident light. A "perfect diffuser" is one that will diffusely reflect all the light that is incident upon it. White objects approximate the properties of a perfect diffuser, especially in the visible region (400–700 nm) of light. A perfect diffuser will reflect each wave length in the visible region fully such that a plot of absolute reflectance ("[R]") for the perfect diffuser verses wave length will result in a horizontal line at [R] equals 1.0, as shown in FIG. 1 (absolute reflectance being the intensity of reflected light to the intensity of the incident light).

Given the difficulty in measuring the intensity of incident light, a more practical method of quantifying the reflectance from a sample surface is to determine a reflectance for the sample surface relative to that of a standard or reference surface. In particular, a relative reflectance ("[% R]") can be calculated as follows:

$$[\% R] = \frac{\text{Intensity Of Reflected Light From Sample}}{\text{Intensity Of Reflected Light From Standard}}$$

Figure 2:
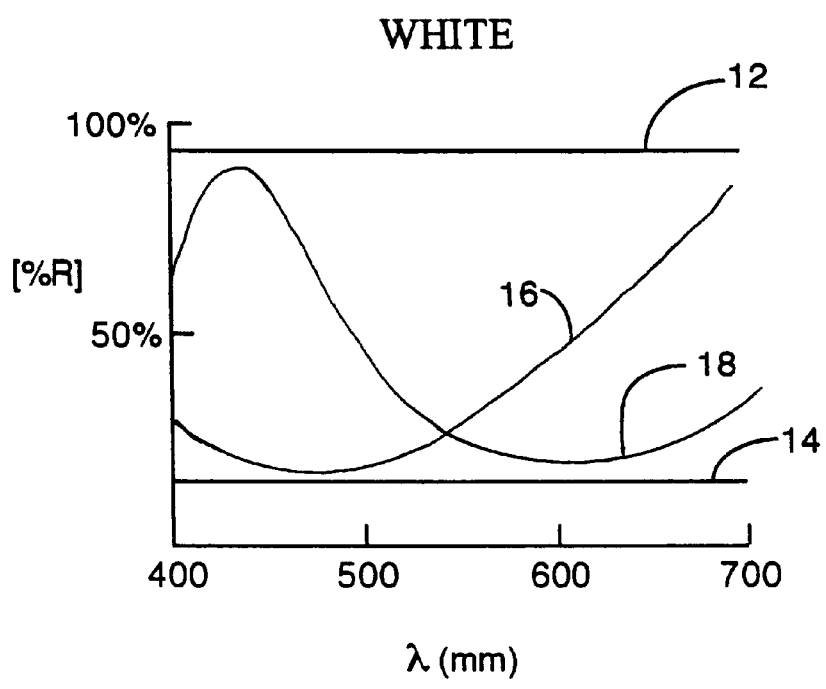
FIG. 2 is a graph showing the spectral reflectance curves for selected colours.

The use of relative reflectance to obtain spectral curves for surfaces liminates the need for measuring the intensity of the incident light. The same standard or reference surface, whose absolute reflectance is known (or approximately known), can be used as a reference to obtain reflectance values for various samples. FIG. 2 illustrates the spectral curves for selected colours in terms of relative reflectance verses wavelength ($\lambda$) for light wavelengths in the visible 400–700 nm range. The spectral curve for a sample white surface, as indicated by reference numeral 12 in FIG. 2, resembles that of a perfect diffuser due to its flatness and high relative reflectance values. A spectral curve for a black surface is indicated by reference number 14 in FIG. 2. As with the spectral curve for the white surface, the spectral curve for the black surface is also flat, however the black surface has very low relative reflectance values. An ideally white surface has a relative reflectance of 100%, whereas an ideally black surface has a relative reflectance of 0% throughout the 400–700 nm range. The spectral curves for colour surfaces lack flatness and reveal peaks and dips in certain regions of the visible light, depending on the colours. For example, the spectral curve for a blue surface (indicated by reference numeral 18) shows a peak in the blue region (450–500 nm) and a dip in the red region (600–700 nm) indicating that a substantial amount of the red component of the incident light is being absorbed by the material. Similarly, the spectral curve for a red surface reveals a maximum relative reflectance in the red region and a minimum relative reflectance in the violet-blue region.

Figure 3:
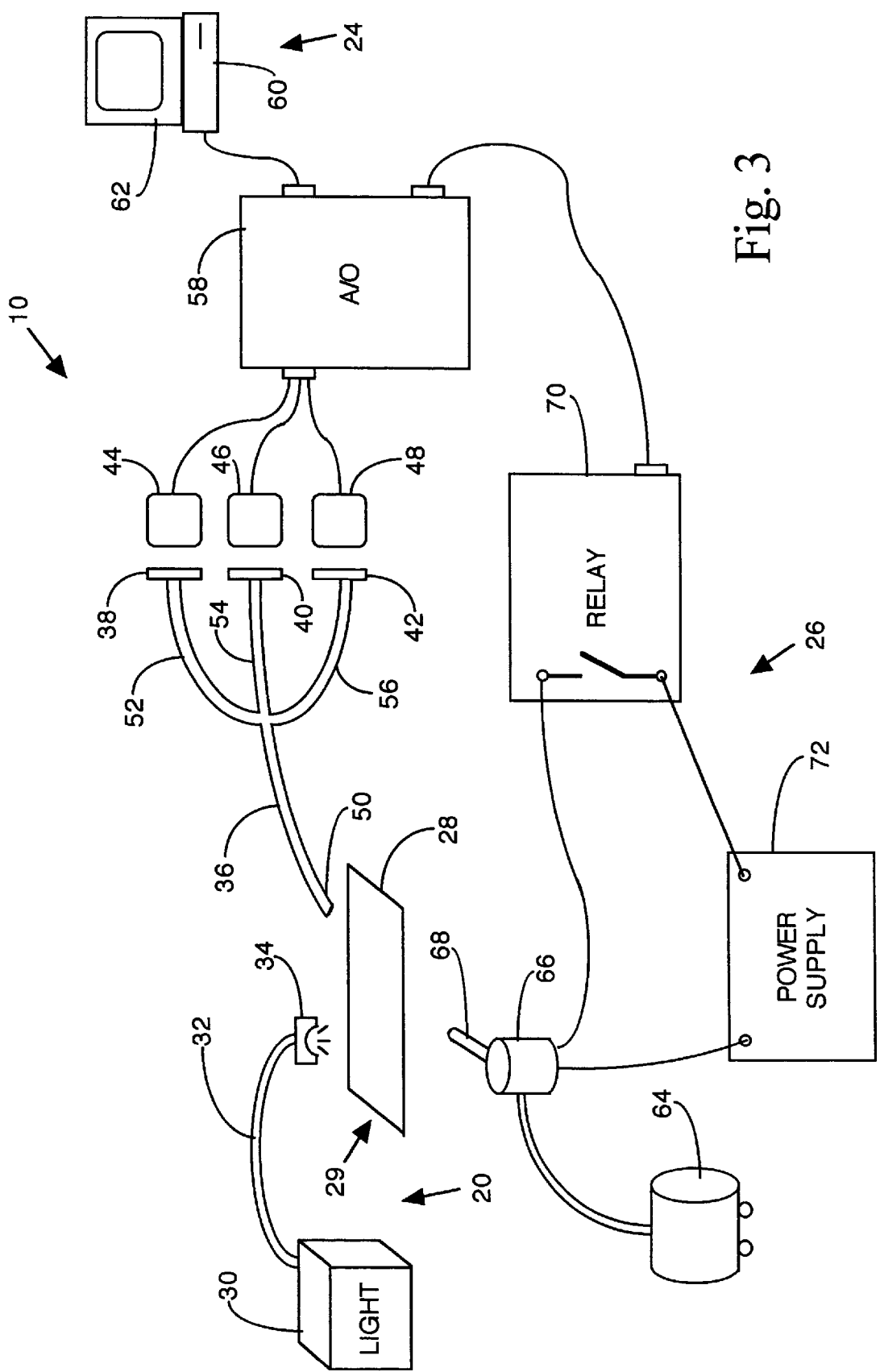
FIG. 3 is a diagram of a device for determining the colour of a workpiece, in accordance with the present invention.

The present invention makes use of the differences in the spectral characteristics between white and non-white surfaces to determine what classification a piece of paper falls in. With reference to FIG. 3, the colour determination system of the present invention (indicated generally by reference numeral 10) includes a light source indicated generally by numeral 20, an optical detection system, indicated generally by numeral 22, a processing system, indicated generally by numeral 24, and an ejection system, indicated generally by numeral 26. The light source 20 is configured to direct a beam of light at a paper sample 28 for which the colour classification is being made, and includes a tungsten halogen light 30, an illuminating fibre bundle 32, and a focusing lens 34.

The tungsten halogen light 30 is a preferred source of illumination as tungsten halogen lights have excellent stability and typically maintain 90% of their initial light output throughout their life. A tungsten halogen light is also a good source of visible radiation (400–700 nm) that is easily detectable by photo diode detectors. However, other light sources could also be used, such as a flourescent light. The fibre optic bundle 32 is preferably made of high grade fused silica with a flexible stainless steel sheathing, and guides the light output by the tungsten halogen light 32 to lens 34. The lens 34 is preferably concave on its outer face in order to cause the light beam delivered by the fibre bundle 32 to converge to a focus. Conveniently, the spacing between the concave lens 34 and the transmitting end of the fibre bundle sheet 32 can be varied by positioning the end of the fibre closer to or away from the lens, thus allowing the diameter of the beam that is directed from the lens 34 to be varied. The lens 34 is supported such that it directs a light beam onto the paper sample 28 which is to be classified as either being white or non-white and which is located at a sampling station 29. The lens 34 is positioned to illuminate the piece of paper normal to the surface of the paper so that the specular reflection will return along the same path as the incident light beam and not interfere extensively with the diffuse reflectance measurements taken by the detection system 22.

The optical detection system 22 functions to receive light diffusely reflected off the paper sample 28, isolate three different spectral components of the reflected light, measure the intensity of each of the three different spectral components, and generate electrical signals representative of the intensity of each of the three different spectral components. In particular, the detection system 22 includes a trifurcated fibre optic bundle 36, filters 38, 40 and 42, and three photo detectors 44, 46 and 48. The trifurcated fiber bundle 36, which acts as a three-way beam splitter, is made of glass with flexible stainless steel sheathing. A receiving end 50 is positioned to receive light reflected from the paper sample 28. In one exemplary example, the fiber bundle 36 receives the reflected light with a cone angle of 64 degrees, thereby making it possible to collect a large amount of the reflected light. Conveniently, the glass fiber bundle 36 blocks radiation below 400 nm and above 1400 nm thus eliminating the need of using further long pass filters to eliminate wavelengths below 400 nm before the reflected light strikes the detectors. Each of the three output branches 52, 54 and 56 of the trifurcated fiber bundle 36 carries light of equal intensity. Trifurcating the reflected light equally allows for determination of the extent of variance in radiant power between the three isolated spectral components of visible light. One suitable trifurcated fiber bundle that can be used in the optical detection system 22 is Model No. 77536 available from Oriel (trade-mark).

The first filter 38 includes a visible bandpass filter and a blue dichroic filter, and is placed between the end of the first branch 52 and the first photo detector 44. The filter 38 cuts off light having a wavelength of greater than 525 nm, allowing only a predominantly blue band (400–525 nm) to pass through and strike the detector 44. As noted above, UV components (<400 nm) are blocked by the fiber bundle 36 prior to reaching the filter 38.

The second filter 40 includes a green dichroic filter and a visible bandpass filter and is positioned between the end of the second branch 54 and the detector 46. The filter 40 cuts off wavelengths less than 475 nm and greater than 650 nm, and has a peak transmission in the wavelength range of 525 nm to 575 nm in the green region. Thus, the filter 40 allows only a predominantly green band to go through and strike the detector 46.

The third filter 42 is positioned between the end of the third branch 56 and the third photo detector 48. The third filter 42 comprises a visible bandpass filter that cuts off infrared radiation ($\lambda$ greater than 900 nm), and has very low transmission in the 700–900 nm range, and a red dichroic filter, which filters out light having a wavelength of less than 600 nm. Accordingly, the third filter 42 allows only a predominantly red band to strike the photo detector 48.

The photo detectors 44, 46 and 48 each include a photo diode and an amplifier for measuring the intensity of the light beams received by the photo detectors and generating an electrical output signal that is proportional to the intensity. Thus, the photo detector 44 produces a voltage signal that is representative of the intensity of blue light diffusely reflected from the paper sample 28, the photo detector 46 produces an electrical output signal that is representative of the intensity of green light diffusely reflected from the paper sample, and the third photo detector 48 produces an electrical output signal that is representative of the intensity of red light diffusely reflected from the paper 28. The analog outputs of the three photo detectors are provided to an A/D convertor 58 which digitizes the three electrical signals for provision to digital computer 60. One example of an acceptable photo diode for use in the present invention is model No. OPT 209 available from BURR-BROWN (trade-mark). The digital computer 60 and A/D convertor 58 are part of the processing system 24.

The digital computer 60, which can be a suitably configured personal computer, is programmed to determine a relative reflectance for each of the three spectral components, determine a mean of the three relative reflectances, determine a standard deviation of the three relative reflectances, and determine, by comparing the mean and standard deviation to predetermine threshold values, whether the paper sample 28 can be classified as white or non-white. In particular, the digital computer 60 is programed to perform these determinations as follows. The digital computer 60 determines a relative reflectance for each of the three spectral components by finding a ratio of the voltage signal generated by each of the detectors 44, 46 and 48 in respect of the light reflected from paper sample 28 and comparing the measured voltages to a preobtained reference voltage for each of the spectral components, as signified by the following three equations:

$$[\%R]\text{blue} = V_b\text{sam}/V_b\text{ref} \quad (1)$$

$$[\%R]\text{green} = V_g\text{sam}/V_g\text{ref} \quad (2)$$

$$[\%R]\text{red} = V_r\text{sam}/V_r\text{ref} \quad (3)$$

where:
[%R] blue; [%R] green and [%R] red are the relative reflectances for the blue, green and red spectral components, respectively;

$V_b$ sam, $V_g$ sam and $V_r$ sam are the magnitudes of the digitized voltage signals generated by the first detector 44, second detector 46, and third detector 48, respectively, in respect of the paper sample 28; and $V_b$ ref, $V_g$ ref and $V_r$ ref are the magnitudes of predetermined reference voltage signals for the blue, green and red spectral components, respectively.

Preferably the predetermined reference voltage signals are stored values which have been obtained as a result of a preproduction calibration step in which the intensity of light reflected from a known white sheet of paper is measured for each of the three spectral regions by detectors 44, 46 and 48, and such values stored by the digital computer 60 as $V_b$ ref, $V_g$ ref and $V_r$ ref, respectively.

Once the digital computer 60 has calculated the relative reflectances in each of the three spectral components for the paper sample 28, it then determines a mean of the three relative reflectances according to the following equation:

$$\overline{[R\%]} = \frac{[\%\,R]\text{blue} + [\%\,R]\text{green} + [\%\,R]\text{red}}{3} \quad (4)$$

where:
[$\overline{R}$] is the mean relative reflectance.

The digital computer then determines, a standard deviation of the relative reflectances for the paper sample 28 according to the following formula:

$$\sigma[R\%] = \sqrt{\frac{([R\%]\text{blue} - \overline{[R\%]})^2 + ([R\%]\text{green} - \overline{[R\%]})^2 + ([R\%]\text{red} - \overline{[R\%]})^2}{2}} \quad (5)$$

As can be seen from the spectral curves in FIG. 2, in terms of relative reflectances, white surfaces exhibit high mean values and very low standard deviations. Black surfaces also exhibit a low standard deviation, but have a mean value that is much lower than that of white surfaces. The mean values of coloured surfaces vary, however they exhibit much higher standard deviation values in comparison to white and black surfaces. Accordingly, the digital computer 60 is configured to classify the piece of paper as either being white or non-white based on comparisons of the calculated mean to a predetermined threshold mean value, and the standard deviation to a predetermined threshold deviation value. In particular, digital computer 60 classifies the paper as white in the event the mean relative reflectance is greater than the predetermined mean value and the standard deviation is less than a predetermined deviation value. If the mean and standard deviation do not met these criteria, the paper sample 28 is classified as non-white. The classification algorithm is set out as follows:

IF {[R
]≧[R
]$_{ref}$ and σ[R%]<σ$_{ref}$} THEN
  SHEET="WHITE"
ELSE
  SHEET "NON-WHITE"
Where:
[R
]ref is the predetermined threshold mean relative reflectance, and
σ$_{ref}$ is the predetermined threshold deviation.

The threshold mean relative reflectance and threshold standard deviation are preferably selected through experimentation dependent on the particular paper products sorted by the device 10. It has been determined that a threshold mean relative reflectance of 50% and a threshold standard deviation of 5.0 provide a high degree of accuracy in separating non-white sheets from white sheets. Other threshold mean reflectance values and threshold standard deviation values could be used depending on how wide or narrow a range was desired to classify recycled paper sheets as "white". It will be appreciated that the lower the threshold mean and the higher the threshold deviation, the broader the classification of "white" paper products would be. Preferably the threshold mean relative reflectance is a value that falls within a range of 50 to 70%, and the threshold standard deviation is a value that falls within a range of 3 to 5.

Once the digital computer 60 classifies the paper sample as non-white or white, it can display its determination on an output screen 62 and furthermore send, depending on whether or not the paper sample is white or non-white, an activation signal via A/D convertor 58 to the ejection system 26. The ejection system 26 is configured to selectively redirect a sample of paper 28 depending on whether the digital computer has classified the paper as white or non-white. The digital computer 60 can be programed to send out an activation signal to redirect the paper 28 if it is non-white if it is desired to redirect non-white paper products, or alternatively can be programed to send out the activation signal when the paper sample is classified as white, in the event that it is desired to redirect white paper products. The ejection system includes an air compressor 64 connected to a normally closed solenoid valve 66 which controls the flow of air from the compressor 64 to an air nozzle 68. Control of the solenoid valve 66 is effected by a relay card 70 which can operatively connect the power supply 72 to the solenoid valve 66. Operation of the relay card 70 is controlled by the actuation signal received via A/D convertor 58 from the digital computer 60. In particular, when the relay card 70 receives the activation signal, it electrically connects the power supply 72 to the solenoid valve 66, causing the solenoid valve 66 to open momentarily thereby allowing a blast of compressed air from compressor 64 to be directed through the nozzle 68 at the paper 28 in order to redirect the sheet of paper 28.

Figure 4:
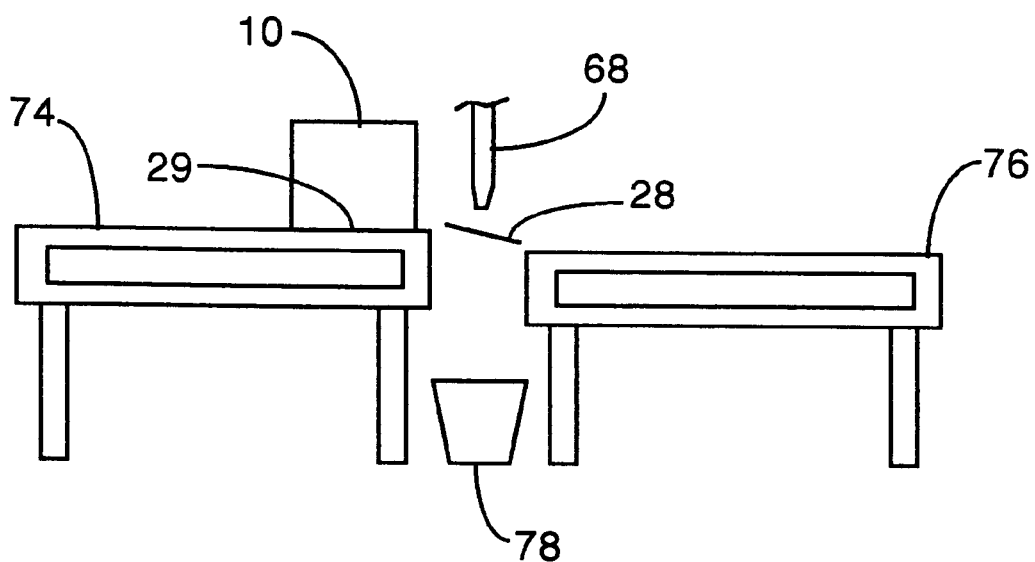
FIG. 4 is a simplified side view of the device of FIG. 3 located in a paper sorting system.

The colour determination system 10 is intended to be used in an automated high speed paper sorting line having, with reference to FIG. 4, a high speed conveyor system for moving sheets of paper to and through the colour determination system 10. In one exemplary embodiment shown in FIG. 4, the conveyor system includes first and second conveyor belts 74 and 76. The first conveyor belt 74 is elevated slightly above, and separated by a space from the second conveyor belt 76. During normal operation, paper pieces moving along the conveyor belt 74 will, after leaving conveyor belt 74 land on the conveyor belt 76 unless redirected by a blast of air from air nozzle 68 into a collection bin 78. The first conveyor belt 74 feeds recyclable paper in single sheets to the sampling station 29 of the colour determination system 10 which determines whether the sheets can be classified as white or non-white and causes air nozzle 68 to selectively redirect sheet samples 28 away from the second conveyor 76 and into the collection basket 78 depending on such determination. The conveyor belt 74 moves at a speed known to the digital computer 60, and accordingly computer 60 is configured to activate the ejection system 26 at an appropriate time to direct a selected paper sample 28 into the waste basket 78. Thus, it will be appreciated that during a particular recycling run the colour determination system 10 continuously classifies a steady stream of paper samples, and selectively redirects paper samples depending on whether they are classified as white or non-white. The determination method used by the digital computer 60 can, with reasonable accuracy, classify paper sheets having a large degree of printed matter thereon as white or non white, and thus functions to determine if the predominant colour of the paper product.

It will be appreciated that the device and method of the present invention could be adopted to sort objects other than paper into one of two possible colour classifications dependent on the dominant colour of such objects.

As will be apparent to those skilled in the art in the light of the foregoing disclosure, many alterations and modifications are possible in the practice of this invention without departing from the spirit or scope thereof. The foregoing description is of the preferred embodiments and is by way of example only, and is not to limit the scope of the invention.

I claim:

1. A paper sorting device for determining if the dominant colour classification of a piece of paper is white or non-white, comprising:

a light source for directing a beam of light at the paper to illuminate the paper;

an optical detection system for receiving light diffusely reflected off the paper, isolating three different spectral components of the same reflected light, measuring the intensity of each of the three different spectral components and generating electrical signals representative of the intensity of each of the three different spectral components, the optical detection system comprising a waveguide having a three-way beam splitter comprising a glass trifurcated fibre bundle that blocks ultraviolet light components, for receiving light diffusely reflected off the paper and directing substantially equal intensities of the reflected light to first, second and third optical outputs;

a first visible bandpass filter comprising a blue dichroic filter and a photo detector positioned at the first optical output to isolate a first spectral component of light emanating therefrom and measure the intensity of the first spectral component;

a second visible bandpass filter comprising a green dichroic filter and a photo detector positioned at the second optical output to isolate a second spectral component of light emanating therefrom and measure the intensity of the second spectral component; and a third visible bandpass filter comprising a red dichroic filter and a photo detector positioned at the third optical output to isolate a third spectral component of light emanating therefrom and measure the intensity of the third spectral component; and a processor responsive to the electrical signals generated by the detection system and operable to (a) determine a relative reflectance for each of the three spectral components;

(b) determine a mean of the three relative reflectances;

(c) determine a standard deviation of the three relative reflectances; and (d) determine, by comparing the mean and standard deviation to predetermined threshold values, whether the paper is white or non-white.

2. The paper sorting device of claim 1 wherein the wavelength ranges of the three spectral components are generally 400 nm–525 nm, 475 nm–650 nm, and 600 nm–800 nm, respectively.

3. The paper sorting device of claim 2 wherein said processor determines the relative reflectance of each of the spectral components by obtaining a ratio of the intensity of reflectance measure for the spectral component versus a predetermined spectral intensity value for the spectral component.

4. The paper sorting device of claim 3 wherein said processor determines that the paper is white when the mean of the relative reflectances exceeds a threshold mean value and the standard deviation of the relative reflectances is below a threshold standard deviation value.

5. The paper sorting device of claim 4 wherein said threshold mean value is generally between 50 and 70 percent and the threshold standard deviation value is generally between 3 and 5.

6. The paper sorting device of claim 1 further including a conveyor system for advancing pieces of paper to and through a sampling station at which the light source is located and an ejection device connected to said processor for selectively redirecting a paper sample from the conveyor system, the processor causing the ejection device to redirect the paper sample from the conveyor system based on the determination of whether the paper sample is white or non-white.

7. A method for classifying paper samples into one of two colour classifications, the two colour classifications being white and non-white, comprising the steps of:

directing a beam of light on a known white object and storing as reference intensity values the measured intensity of the light diffusely reflected from the white object in each of the three spectral components, the first spectral component corresponding to the colour blue, the second spectral component corresponding to the colour green, and the third spectral component corresponds to the colour red;

directing a beam of visible light on the paper sample to illuminate the paper sample;

measuring the intensities of the three different spectral components in the light which is diffusely reflected off the paper sample, from the same diffusely reflected light;

determining, based on the measured intensities, a relative reflectance for each of the spectral components, the relative reflectance that is determined for each of the spectral components being a ratio of the measured intensity of light reflected to the reference intensity value;

determining a mean of the three relative reflectances;

determining a standard deviation of the three relative reflectances; and comparing the mean and standard deviation to predetermined values and classifying the paper sample as falling within one of the two colour classifications based on the comparison results.

8. A method according to claim 7 wherein the paper sample is classified as white only if the mean reflectance exceeds a predetermined percentage and the standard deviation is less than a predetermined acceptable deviation.

* * * * *